United States Patent
Murashima et al.

(10) Patent No.: US 9,645,322 B2
(45) Date of Patent: May 9, 2017

(54) OPTICAL PROBE FOR OPTICAL COHERENCE TOMOGRAPHY AND MANUFACTURING METHOD THEREFOR

(71) Applicant: Sumitomo Electric Industries, Ltd., Osaka-shi (JP)

(72) Inventors: Kiyotaka Murashima, Yokohama (JP); Mitsuharu Hirano, Yokohama (JP)

(73) Assignee: Sumitomo Electric Industries, Ltd., Osaka-shi (JP)

( * ) Notice: Subject to any disclaimer, the term of this patent is extended or adjusted under 35 U.S.C. 154(b) by 0 days.

(21) Appl. No.: 15/152,652

(22) Filed: May 12, 2016

(65) Prior Publication Data

US 2016/0320564 A1    Nov. 3, 2016

Related U.S. Application Data

(63) Continuation of application No. PCT/JP2014/078303, filed on Oct. 24, 2014.

(30) Foreign Application Priority Data

Nov. 18, 2013 (JP) .................................. 2013-237925

(51) Int. Cl.
   *G02B 6/36* (2006.01)
   *G02B 6/255* (2006.01)
   (Continued)

(52) U.S. Cl.
   CPC ......... *G02B 6/3624* (2013.01); *G02B 6/2551* (2013.01); *A61B 1/00165* (2013.01);
   (Continued)

(58) Field of Classification Search
   CPC .................................................. G02B 6/3624
   See application file for complete search history.

(56) References Cited

U.S. PATENT DOCUMENTS 6,445,939 B1 * 9/2002 Swanson ............... A61B 5/0066
   385/33
7,805,034 B2 * 9/2010 Kato .................... A61B 5/0066
   385/147
(Continued)

FOREIGN PATENT DOCUMENTS

EP    1136854 A2    9/2001
EP    1659429 A1    5/2006
(Continued)

OTHER PUBLICATIONS

"FITEL® Fusion Splicers & Tools Catalog," Furukawa Electric, vol. 4, Sep. 15, 2010.
(Continued)

*Primary Examiner* — Jerry Rahll
(74) *Attorney, Agent, or Firm* — Venable LLP; Michael A. Sartori; Laura G. Remus

(57) ABSTRACT

To provide an optical probe for OCT and a method of manufacturing the optical probe that can reduce reflected light generated at a boundary portion between an optical fiber and a lensed fiber. An optical probe for OCT includes an optical fiber that transmits irradiation light and back-scattered light and a lensed fiber that is fusion spliced to an end face of the optical fiber, that emits irradiation light toward the inside of a living body while collimating the irradiation light, and that collects and guides back-scattered light to the end face of the optical fiber. A refractive index adjusting material is added to the lensed fiber, and the refractive index adjusting material is diffused in an end part of the optical fiber.

7 Claims, 17 Drawing Sheets

(51) Int. Cl.

| | | |
|---|---|---|
| A61B 1/00 | (2006.01) | |
| A61B 1/07 | (2006.01) | |
| A61B 5/00 | (2006.01) | |
| G02B 6/32 | (2006.01) | |
| G01B 9/02 | (2006.01) | |
| G02B 6/26 | (2006.01) | |
| G02B 6/028 | (2006.01) | |

(52) U.S. Cl.
CPC ............... *A61B 1/07* (2013.01); *A61B 5/0066* (2013.01); *A61B 5/6852* (2013.01); *A61B 2562/0233* (2013.01); *G01B 9/02091* (2013.01); *G02B 6/0281* (2013.01); *G02B 6/2552* (2013.01); *G02B 6/262* (2013.01); *G02B 6/32* (2013.01)

(56) References Cited

U.S. PATENT DOCUMENTS

| | | | | |
|---|---|---|---|---|
| RE45,512 E | * | 5/2015 | Tearney | A61B 5/0066 385/100 |
| 2002/0151823 A1 | * | 10/2002 | Miyata | A61B 5/6851 600/585 |
| 2003/0012526 A1 | * | 1/2003 | Riis | G02B 6/2551 385/96 |
| 2004/0114886 A1 | * | 6/2004 | Christensen | G02B 6/2552 385/96 |
| 2004/0161210 A1 | * | 8/2004 | Chandan | G02B 6/262 385/96 |
| 2006/0067620 A1 | | 3/2006 | Shishkov et al. | |
| 2009/0190883 A1 | * | 7/2009 | Kato | A61B 5/0066 385/33 |
| 2011/0316029 A1 | * | 12/2011 | Maruyama | A61B 5/0066 257/98 |
| 2012/0002919 A1 | | 1/2012 | Liu | |
| 2012/0073331 A1 | * | 3/2012 | Tachikura | G02B 6/255 65/439 |
| 2012/0328241 A1 | | 12/2012 | Shishkov et al. | |
| 2012/0330101 A1 | * | 12/2012 | Brennan | A61B 1/00096 600/177 |
| 2013/0023760 A1 | | 1/2013 | Liu et al. | |
| 2014/0275986 A1 | * | 9/2014 | Vertikov | A61B 5/061 600/424 |
| 2015/0245768 A1 | * | 9/2015 | Hasegawa | G01B 9/0205 356/479 |

FOREIGN PATENT DOCUMENTS

| | | |
|---|---|---|
| JP | 4-118607 A | 4/1992 |
| JP | 9-236721 B2 | 9/1997 |
| JP | 3355575 B2 | 10/2002 |
| JP | 2003-515758 A | 5/2003 |
| JP | 2006-315935 A | 11/2006 |
| JP | 2008-040252 A | 2/2008 |
| JP | 2008-183208 A | 8/2008 |
| JP | 2009-178229 A | 8/2009 |
| JP | 2011-217973 A | 11/2011 |
| JP | 2013-40070 A | 2/2013 |
| JP | 2013-202295 A | 10/2013 |

OTHER PUBLICATIONS

Michael A. Choma et al., "Sensitivity advantage of swept source and Fourier domain optical coherence tomography," Opt. Express 11, 2003, pp. 2183-2189.

International Search Report in PCT International Application No. PCT/JP2014/078303, dated Feb. 10, 2015.

Extended European Search Report in counterpart European Patent Application No. 14862146.9 dated Nov. 11, 2016.

* cited by examiner

OPTICAL PROBE FOR OPTICAL COHERENCE TOMOGRAPHY AND MANUFACTURING METHOD THEREFOR

CROSS REFERENCES TO RELATED APPLICATIONS

The present application is a continuation application of International Application No. PCT/JP2014/078303, filed Oct. 24, 2014, which claims priority to Japanese Patent Application No. 2013-237925, filed Nov. 18, 2013. The contents of these applications are incorporated herein by reference in their entirety.

TECHNICAL FIELD

The present invention relates to an optical probe for optical coherence tomography and a method of manufacturing the optical probe.

BACKGROUND ART

Fusion splicers for optical fibers are described in "FITEL (registered trademark) Fusion Splicers & Tools Catalog", Furukawa Electric, Volume 4, September 2010 (NPL 1). Two optical fibers are connected to each other by butting ends the optical fibers against each other and heat-fusing the ends together. The sensitivity of optical coherence tomography (OCT) is described in Michael A. Choma, "Sensitivity advantage of swept source and Fourier domain optical coherence tomography, Opt. Express 11, 2183-2189 (2003)" (NPL 2).

SUMMARY OF INVENTION

Technical Problem

An object of the present invention is to provide an optical probe for optical coherence tomography and a method of manufacturing the optical probe that can reduce reflected light generated at a boundary portion between an optical fiber and a lensed fiber.

Solution to Problem

To achieve the object, there is provided an optical probe for optical coherence tomography including an optical fiber that transmits irradiation light and back-scattered light; and a lensed fiber that is fusion spliced to one end of the optical fiber, that emits the irradiation light toward an object to be measured while collimating the irradiation light, and that collects and guides back-scattered light from the object to be measured to the one end of the optical fiber. A material for adjusting a refractive index is added to the lensed fiber, and the material is diffused in an end part of the optical fiber including the one end.

In the optical probe for optical coherence tomography according to the present invention, intensity of light reflected at a boundary portion between the one end of the optical fiber and the lensed fiber, the intensity being measured at the other end of the optical fiber, may be less than −60 dB/nm, may be −70 dB/nm or less, or may be −80 dB/nm or less with respect to Fresnel reflection intensity when the one end of the optical fiber is in contact with air. In the optical probe for optical coherence tomography according to the present invention, a refractive index of a core region of the optical fiber gradually may become closer to a refractive index of the lensed fiber as a distance from the lensed fiber decreases.

As another aspect of the present invention, there is provided a method of manufacturing an optical probe for optical coherence tomography, the method including a step of fusion splicing one end of an optical fiber and a lensed fiber together and diffusing a material included in the lensed fiber in an end part of the optical fiber by using heat generated in fusion splicing. In the step, the one end of the optical fiber and the lensed fiber are fusion spliced together while measuring intensity of light reflected at a boundary portion between the one end of the optical fiber and the lensed fiber at the other end of the optical fiber.

Advantageous Effects of Invention

With the optical probe for optical coherence tomography and the method of manufacturing the optical probe according to the present invention, reflected light generated at a boundary portion between an optical fiber and a lensed fiber can be reduced.

DESCRIPTION OF EMBODIMENTS

Figure 1:
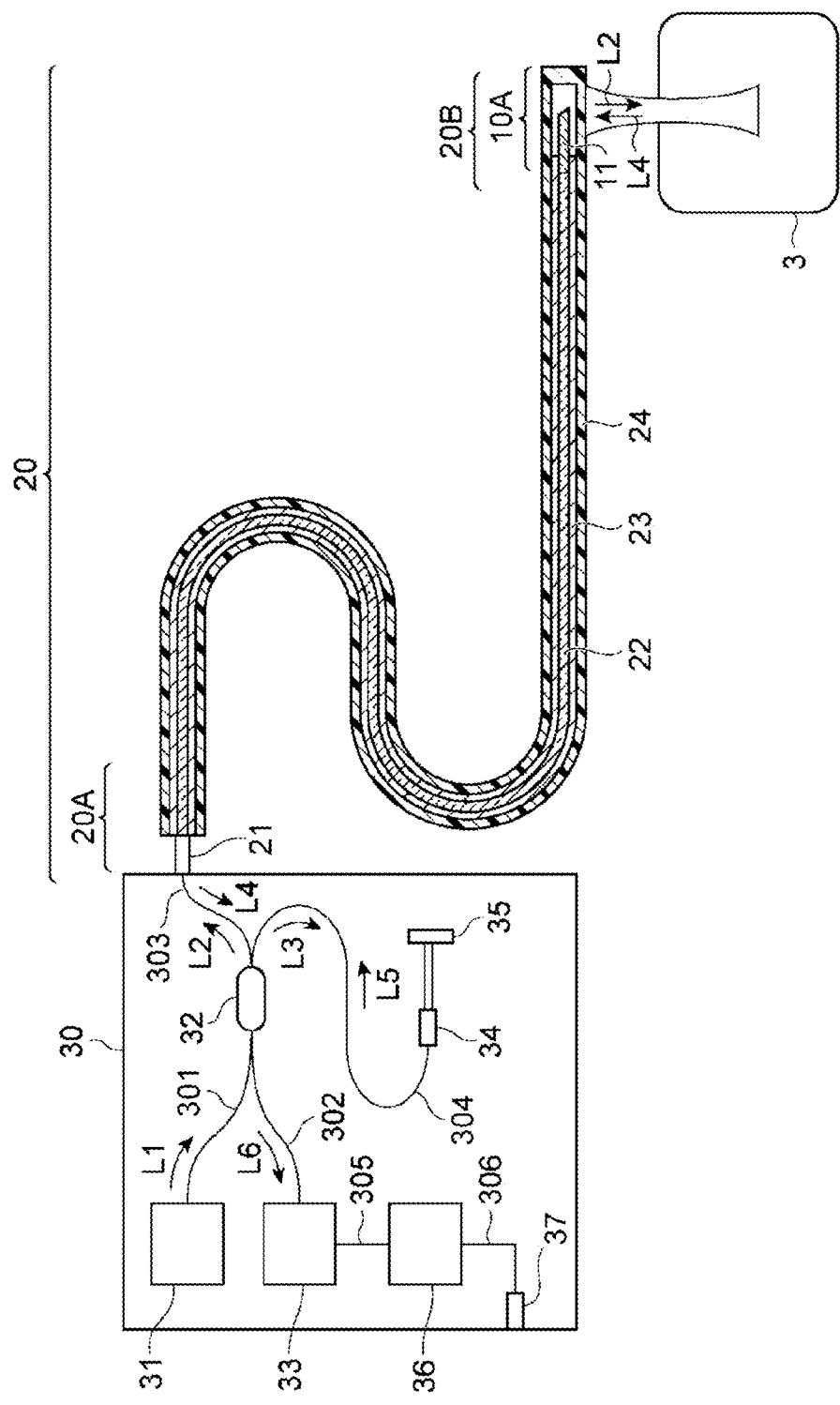
FIG. 1 is a conceptual diagram of an OCT system including an optical probe for OCT according to an embodiment of the present invention.

OCT is a technology for obtaining a tomography image by irradiating the inside of an object with irradiation light and by causing interference between the irradiation light and back-scattered light from the inside of the object. By using this technology, a tomography image of a living object can be obtained by inserting a catheter into a lumen of the living object and by irradiating the lumen with light emitted from an optical probe disposed at the distal end of the catheter. The optical probe includes an optical fiber, which transmits irradiation light and back-scattered light, and a lensed fiber, which is fusion spliced to an end of the optical fiber.

Such an OCT system needs to detect faint back-scattered light from the living object with high accuracy. However, a part of irradiation light may be reflected at a fusion spliced portion between the optical probe and the lensed fiber, and the reflected light may be mixed with back-scattered light as noise. Such reflected light becomes an obstacle for detecting faint back-scattered light with high accuracy.

For example, even when optical fibers of the same type are connected to each other by using fusion splicers described in NPL 1, reflected light having an intensity in the range of −60 dB to −70 dB with respect to incident light is generated at the boundary portion between the optical fibers. In an optical probe of an OCT system, an optical fiber and a lensed fiber, which considerably differ from each other in numerical aperture and core refractive index, are connected to each other. Therefore, considerably intense reflected light is generated at the boundary portion. For example, the OCT system described in NPL 2 detects back-scattered light with a high sensitivity, which is 100 dB or higher. With such a high sensitivity, reflected light from the boundary portion is inevitably detected.

Hereinafter, specific examples of an optical probe for OCT and a method of manufacturing the optical probe according to an embodiment of the present invention will be described with reference to the drawings. The scope of the present invention, which is represented by the claims, is not limited to these examples, and it is intended that the scope encompass all modifications within the meaning of the claims and the equivalents thereof. In the following description, the same elements in the drawings will be denoted by the identical numerals and redundant descriptions of such elements will be omitted.

FIG. 1 is a conceptual diagram of an OCT system 1 including an optical probe 10A for OCT according to the embodiment of the present invention. The OCT system 1 includes a catheter 20 and a detector 30 and obtains a tomographic image of a living object 3. The catheter 20 includes one end part 20A and the other end part 20B in the longitudinal direction. The end part 20A includes a connector 21. The catheter 20 is optically connected to the detector 30 through the connector 21. The end part 20B includes the optical probe 10A for OCT (hereinafter, simply referred to as "optical probe 10A").

The catheter 20 includes an optical fiber 22, a rotating force transmitting member (torque wire) 23, and an exterior member 24. The rotating force transmitting member 23 is tubular, contains the optical fiber 22 in a hollow portion thereof, and transmits a rotating force from the connector 21 to the end part 20B. The exterior member 24 is tubular and surrounds the optical fiber 22 and the rotating force transmitting member 23. The exterior member 24, which is the outermost portion of the catheter 20, does not rotate and is stationary. For example, the optical fiber 22 is a single-mode optical fiber that includes a glass fiber and a resin cover that covers the glass fiber. The glass fiber includes a core region having a high refractive index and a cladding region having a low refractive index. A lensed fiber 11 is attached to one end of the optical fiber 22 opposite to the connector 21.

The detector 30 includes a light source 31, a 2×2 optical coupler 32, an optical detector 33, an optical terminal 34, a mirror 35, an analyzer 36, and an output port 37. The detector 30 includes waveguides 301 to 304. The waveguide 301 optically couples the light source 31 and the 2×2 optical coupler 32 to each other. The waveguide 302 optically couples the 2×2 optical coupler 32 and the optical detector 33 to each other. The waveguide 303 optically couples the 2×2 optical coupler 32 and the connector 21 to each other. The waveguide 304 optically couples the 2×2 optical coupler 32 and the optical terminal 34 to each other. The optical detector 33 and the analyzer 36 are electrically connected to each other through a signal wire 305, and the analyzer 36 and the output port 37 are electrically connected to each other through a signal wire 306.

The light source 31 generates low coherence light L1. After being guided along the waveguide 301, the low coherence light L1 is split by the 2×2 optical coupler 32 into irradiation light L2 and reference light L3.

After being guided along the waveguide 303, the irradiation light L2 passes through the connector 21 and enters the other end of the optical fiber 22 in the catheter 20. After exiting from the one end of the optical fiber 22, the irradiation light L2 is deflected by an inclined surface formed at an end of the lensed fiber 11; and the living object 3, such as a blood vessel, is irradiated with the irradiation light L2. The living object 3 reflects and deflects the irradiation light L2, thereby generating back-scattered light L4. The back-scattered light L4 passes through the lensed fiber 11 and propagates through the optical fiber 22 in a direction opposite to the direction of the irradiation light L2. After entering the waveguide 303 through the connector 21, the back-scattered light L4 is guided into the 2×2 optical coupler 32, to the waveguide 302, and into the optical detector 33. After passing through the waveguide 304, the reference light L3 is emitted from the optical terminal 34 and reflected by the mirror 35 to become returned reference light L5. The returned reference light L5 passes through the optical terminal 34 and the waveguide 304, and is guided into the 2×2 optical coupler 32.

The back-scattered light L4 and the returned reference light L5 interfere with each other in the 2×2 optical coupler 32, thereby generating interference light L6. The interference light L6 is guided from the 2×2 optical coupler 32, to the waveguide 302, and into the optical detector 33.

The optical detector 33 detects the intensity (spectrum) of the interference light L6 corresponding to wavelength. A detection signal representing the spectrum of the interference light L6 is input to the analyzer 36 through the signal wire 305. The analyzer 36 analyzes the spectrum of the interference light L6 and calculates the profile of reflection efficiency at each point in the living object 3. On the basis of the calculation result, the analyzer 36 obtains a tomographic image of the living object 3 and outputs an image signal representing the tomographic image. The image signal is output from the output port 37 to the outside of the OCT system 1.

Figure 2:
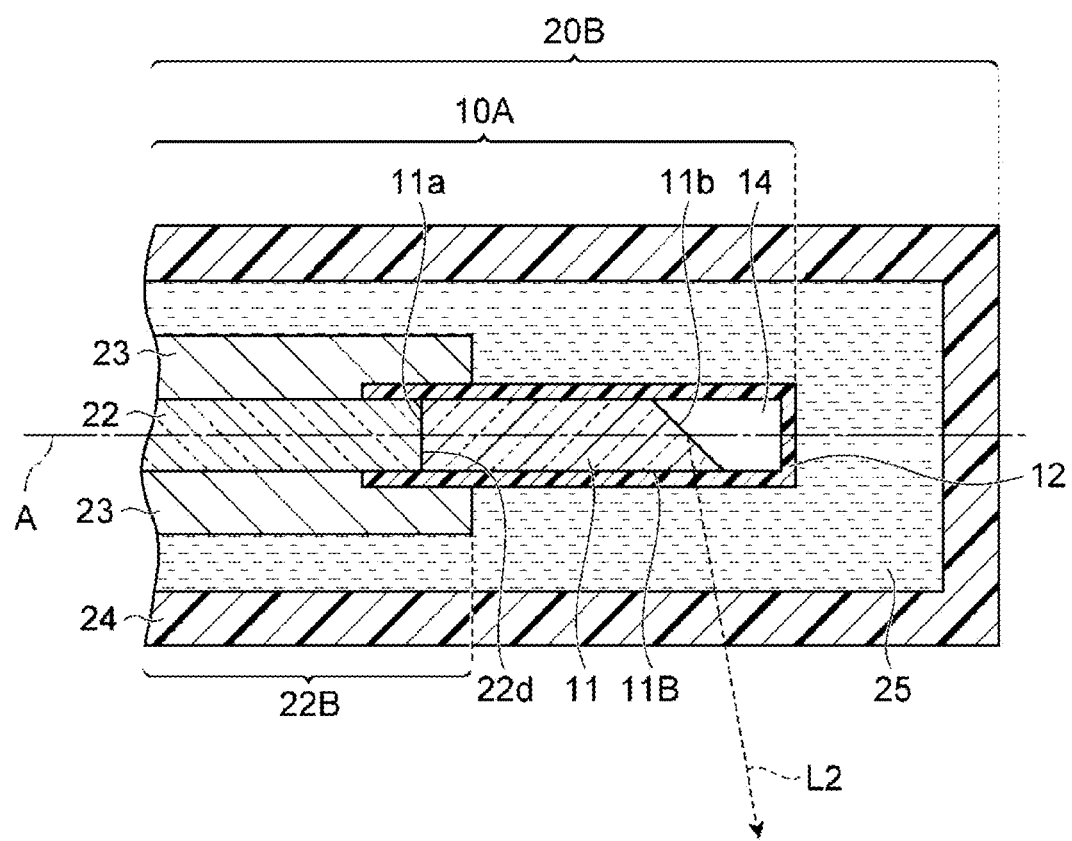
FIG. 2 is a conceptual diagram of the optical probe for OCT according to the embodiment of the present invention.

FIG. 2 is a conceptual diagram of the optical probe 10A. The optical probe 10A is a portion of the end part 20B of the catheter 20 and is contained in the exterior member 24. The optical probe 10A includes an end part 22B of the optical fiber 22, including one end face $22d$ of the optical fiber 22 in a direction along the optical axis A of the optical fiber 22.

The end part 22B of the optical fiber 22 is contained in a hollow portion of the rotating force transmitting member 23 and is fixed to the rotating force transmitting member 23 with an adhesive. A space between the rotating force transmitting member 23 and the exterior member 24 may be filled with a buffering liquid 25 or air. For example, saline, matching oil, or the like may be used as the buffering liquid 25.

The optical probe 10A further includes the lensed fiber 11 and a cap 12. The refractive index of the inside of the lensed fiber 11 is adjusted so that the lensed fiber 11 has a refractive index profile of a graded index (GRIN) lens in a plane perpendicular to the axis A. The lensed fiber 11 has a connecting surface 11a and a deflecting surface 11b, which are arranged in a direction along the optical axis A. The deflecting surface 11b has an angle with respect to the direction along the optical axis A. The lensed fiber 11 is fusion spliced to the end face 22d of the optical fiber 22 via the connecting surface 11a. The lensed fiber 11 collimates the irradiation light L2 emitted from the end face 22d and deflects the irradiation light L2 sideways (in a direction intersecting the optical axis A) using the deflecting surface 11b. Moreover, the lensed fiber 11 deflects the back-scattered light L4, which has returned from the inside of the living object 3, toward the end face 22d of the optical fiber 22 using the deflecting surface 11b; collects the back-scattered light L4; and guides the back-scattered light L4 toward the end face 22d. With the lensed fiber 11, the irradiation light L2 can be focused on a small spot, and a tomography image of a very small region in the living object 3 can be obtained.

A low refractive index medium 14 is disposed adjacent to the deflecting surface 11b of the lensed fiber 11. The refractive index of the low refractive index medium 14 is lower than the refractive index of an end part 11B of the lensed fiber 11, including the deflecting surface 11b. Thus, the deflecting surface 11b is a total reflection surface. As the low refractive index medium 14, for example, air is suitable.

The angle between a normal to the deflecting surface 11b and the optical axis A is, for example, greater than 45° and less than or equal to 55°. When the angle is not 45°, the irradiation light L2 can be prevented from becoming perpendicularly incident on the exterior member 24, and reflected light from the exterior member 24 or the like can be prevented from becoming mixed with the back-scattered light L4 from the living object 3. When the angle is less than or equal to 55°, a decrease in the intensity of the back-scattered light L4 that enters the lensed fiber can be prevented.

The cap 12 hermetically surrounds the deflecting surface 11b and the low refractive index medium 14 so that a liquid, such as the buffering liquid 25, may not contact the deflecting surface 11b of the lensed fiber 11. The cap 12 extends to a hollow portion of the rotating force transmitting member 23. The cap 12 is made of a material that transmits the irradiation light L2 deflected by the lensed fiber 11 and that transmits the back-scattered light L4 returned from the living object 3, that is, a material that is transparent with respect to the wavelengths of the irradiation light L2 and the back-scattered light L4. However, preferably, the refractive index difference between the cap 12 and the lensed fiber 11 is small so that Fresnel reflection loss, which occurs due to the refractive index difference when the irradiation light L2 and the back-scattered light L4 pass through the boundary portion between the cap 12 and the lensed fiber 11, can be suppressed. As the material of the cap 12, for example, polyethylene terephthalate (PET) or polyethylene naphthalate (PEN), or the like is preferable.

Figure 3A:
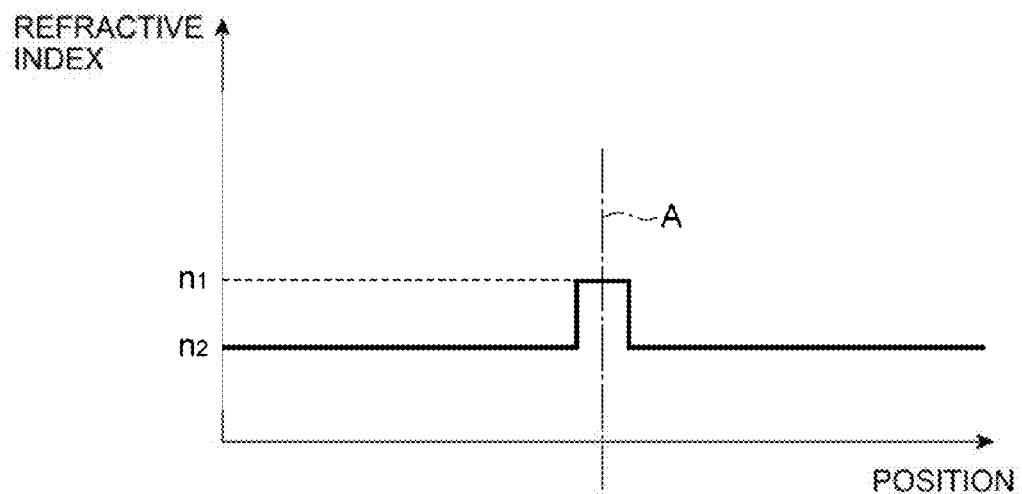
FIG. 3A is a graph representing a typical example of the refractive index profile of an optical fiber and FIG. 3B is a graph representing a typical example of the refractive index profile of a lensed fiber.
Figure 3B:
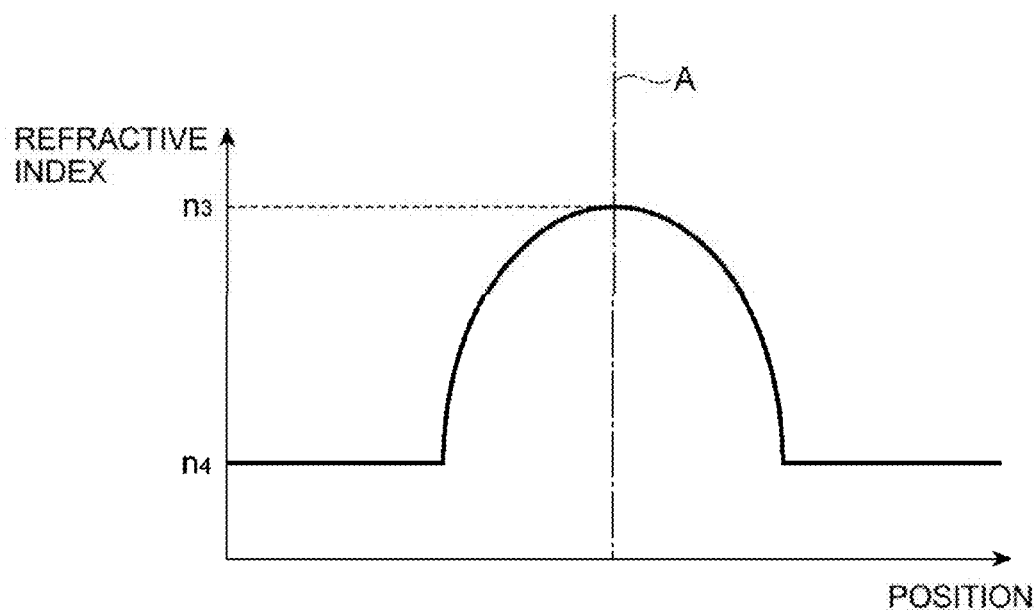

FIG. 3A is a graph representing the refractive index profile of the optical fiber 22, and FIG. 3B is a graph representing the refractive index profile of the lensed fiber 11. In FIGS. 3A and 3B, the vertical axis represents the refractive index, and the horizontal axis represents the position in a plane perpendicular to the optical axis A.

When the optical fiber 22 is a single-mode fiber, as illustrated in FIG. 3A, the refractive index of the optical fiber 22 is $n_1$ in the core region including the optical axis A and is $n_2$ in the cladding region surrounding the core region (where $n_1 > n_2$). The refractive index $n_1$ of the core region is greater than $n_2$ by, for example 0.4% in terms of relative refractive index difference $(n_1 - n_2)/n_1$. As illustrated in FIG. 3B, the refractive index of the lensed fiber 11 is $n_3$ on the optical axis A in the core region and is $n_4$ in the cladding region surrounding the core region (or in the outermost layer of the core region, if the lensed fiber is designed to have no cladding region) (where $n_3 > n_4$). Usually, a lensed fiber in which $n_3$ is greater than $n_4$ by about 2.4% in terms of relative refractive index difference $(n_3 - n_4)/n_3$ is used. Accordingly, if the optical fiber 22 and the lensed fiber 11 are simply connected to each other, the refractive index difference at the boundary portion between the optical fiber 22 and the lensed fiber 11 is 2%.

In general, at the boundary surface between a medium having a refractive index $n_1$ and a medium having a refractive index $n_3$, reflection R represented by the following expression occurs.

$$R = \left\{ \frac{n_3 - n_1}{n_3 + n_1} \right\}^2$$

For example, when $(n_3 - n_1)/n_1$ is 2%, if the optical fiber 22 and the lensed fiber 11 are simply connected to each other without taking any measures, the reflection R=−40 dB, and extremely intense reflected light may be generated. Accordingly, the present embodiment is configured as follows.

Figure 4A:
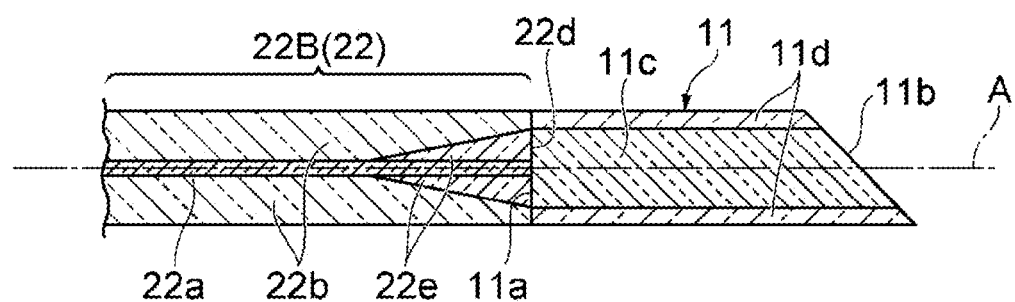
FIG. 4A is a conceptual diagram showing the structure of the vicinity of a boundary portion between an end part of the optical fiber and the lensed fiber.

FIG. 4A is a conceptual diagram of the vicinity of the boundary portion between the end part 22B of the optical fiber 22 and the lensed fiber 11, showing a section along the optical axis A. As described above, the optical fiber 22 includes a core region 22a and a cladding region 22b, and the lensed fiber 11 includes a core region 11c and a cladding region 11d. (There is a case where the lensed fiber 11 does not have the cladding region 11d.) The refractive index $n_3$ of the core region 11c is greater than the refractive index $n_1$ of the core region 22a, and the diameter of the core region 11c is greater than the diameter of the core region 22a.

Figure 4B:
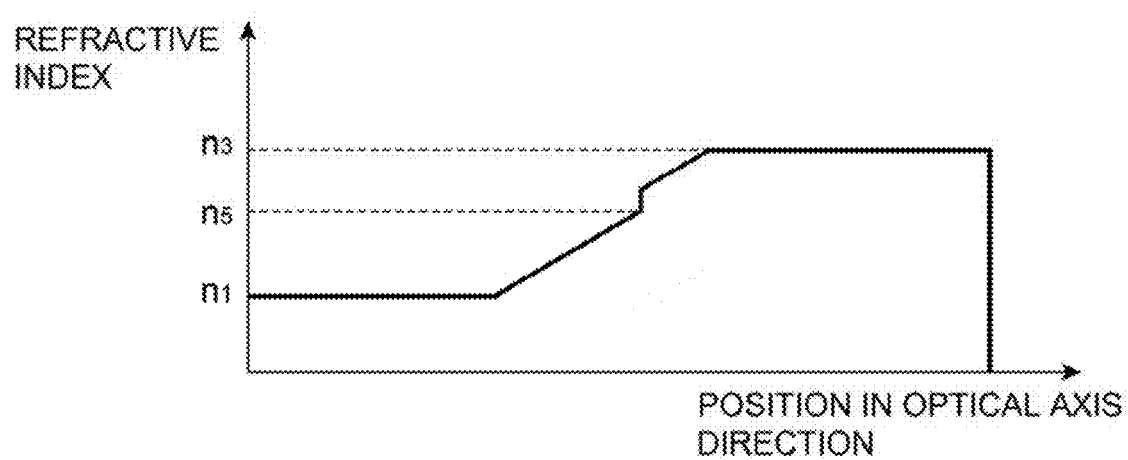
FIG. 4B is a graph representing the refractive index profile of the end part of the optical fiber and the lensed fiber along the optical axis.

FIG. 4B is a graph representing the refractive index profile of the end part 22B of the optical fiber 22 and the lensed fiber 11 along the optical axis A. In FIG. 4B, the horizontal axis represents the position in a direction along the optical axis A so as to correspond to FIG. 4A, and the vertical axis represents the refractive index. As illustrated in FIG. 4B, in the present embodiment, the refractive index of the end part 22B of the core region 22a of the optical fiber 22 becomes closer to the refractive index $n_3$ of the core region 11c of the lensed fiber 11 as the distance from the lensed fiber 11 decreases. To be specific, the refractive index of the core region 22a monotonously increases from a certain position in the direction along the optical axis A toward the end face 22d; and the refractive index of the core region 22a at the end face 22d, that is, at the boundary portion between the optical fiber 22 and the lensed fiber 11, is $n_5$ (>$n_1$). Thus, the refractive index difference at the boundary portion between the core region 22a of the optical fiber 22 and the core region of the lensed fiber 11 is reduced, and reflected light generated at the boundary portion can be effectively reduced.

Preferably, the difference between the refractive index $n_5$ and the refractive index $n_3$ of the core region 11c is extremely small. Thus, reflected light generated at the boundary portion between the optical fiber 22 and the lensed fiber 11 can be more effectively reduced.

A material for adjusting a refractive index (such as Ge) is added to the core region 11c of the lensed fiber 11. The end part 22B of the optical fiber 22 has the refractive index profile illustrated in FIG. 4B, because the refractive index adjusting material is diffused in the end part 22B of the optical fiber 22. Due to the diffusion, the diameter of the core region 22a in the end part 22B of the optical fiber 22 gradually increases as the distance from the lensed fiber 11 decreases (see a core region 22e in the figure). Thus, the propagation loss of the back-scattered light L4 at the boundary portion between the optical fiber 22 and the lensed fiber 11 can be also reduced.

The optical probe 10A has the following advantages. In the optical probe 10A, a material (Ge) for refractive index adjustment, which is added to the core region 11c of the lensed fiber 11, is diffused in the end part 22B of the optical fiber 22. Such a diffusion is appropriately realized, for example, by controlling temperature and time when fusion splicing the optical fiber 22 and the lensed fiber 11 together. Due to such a diffusion, the end part 22B of the optical fiber 22 has a sloped refractive index profile, that is, a profile in which the refractive index of the core region 22a of the optical fiber 22 gradually becomes closer to the refractive index of the core region 11c of the lensed fiber 11 as the distance from the lensed fiber 11 decreases. Accordingly, the refractive index difference at the boundary portion between the optical fiber 22 and the lensed fiber 11 is reduced, and reflected light generated at the boundary portion can be effectively reduced.

In the present embodiment, the intensity of light reflected at the boundary portion between one end (the end face 22d) of the optical fiber 22 and the lensed fiber 11, which is measured at the other end of the optical fiber 22, may be −70 dB/nm or less, or may be −80 dB/nm or less, with respect to Fresnel reflection intensity when the end face 22d of the optical fiber 22 is in contact with air, as shown in examples described below. Thus, the effect of reflected light generated at the boundary portion between the optical fiber 22 and the lensed fiber 11 on the detection result of the back-scattered light L4 can be effectively suppressed, and high-accuracy OCT measurement can be realized.

EXAMPLES

Figure 5:
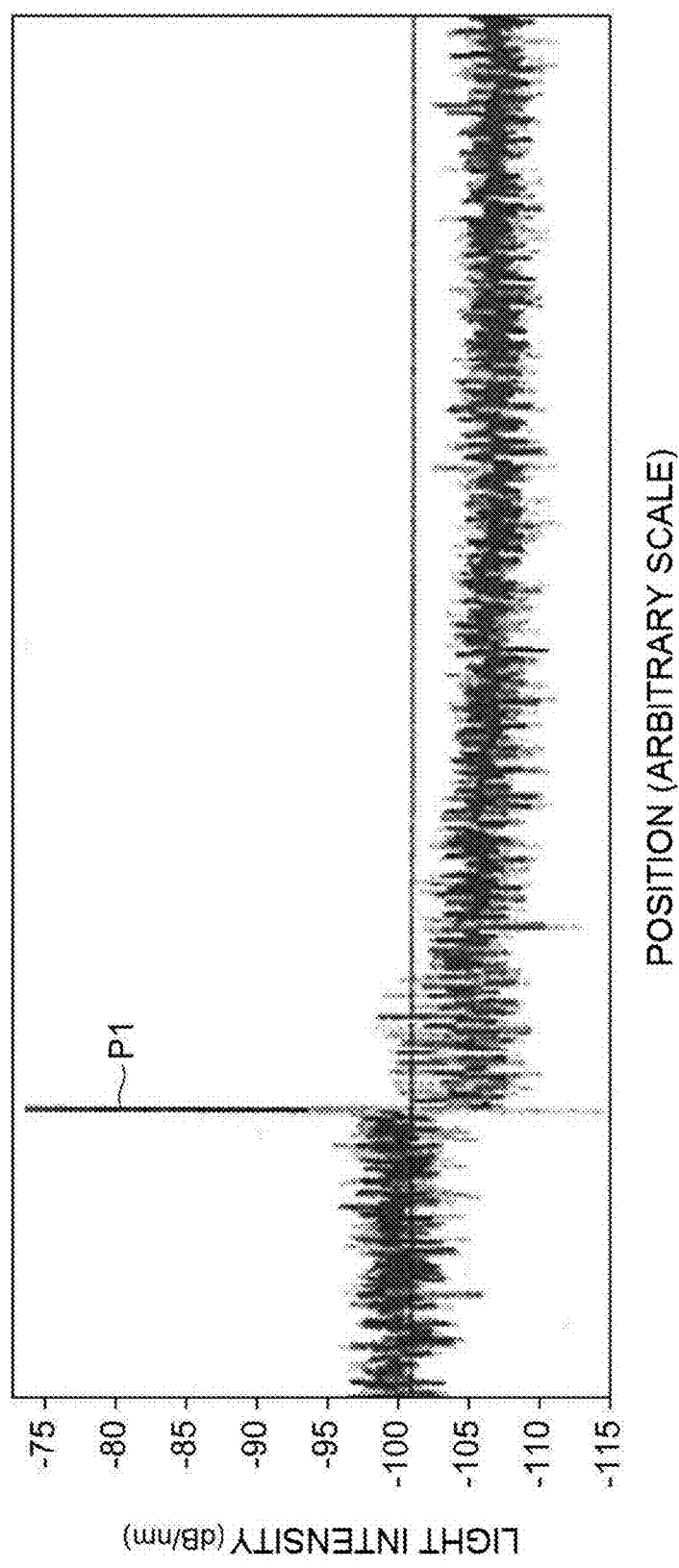
FIG. 5 is a graph representing reflected light intensity at the boundary portion between the optical fiber and the lensed fiber.
Figure 6:
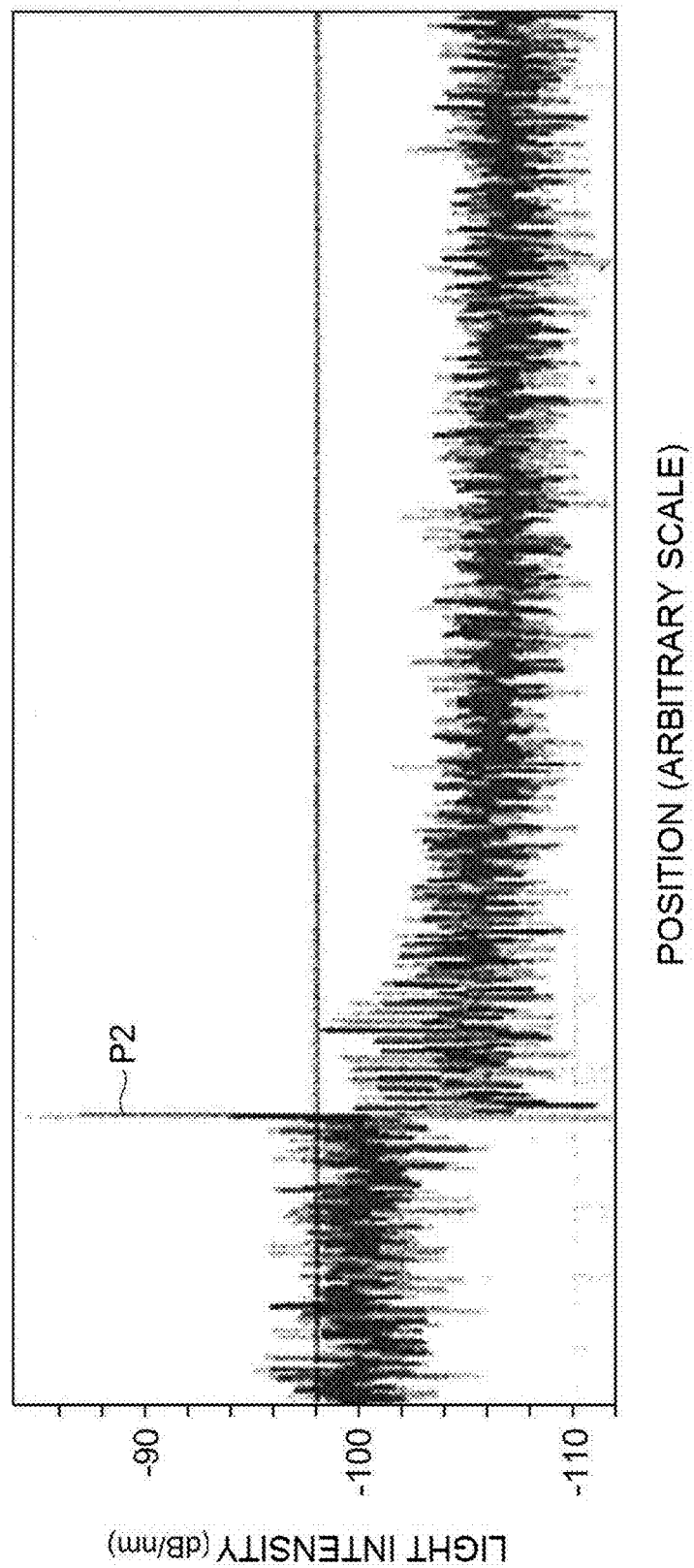
FIG. 6 is a graph representing reflected light intensity at the boundary portion between the optical fiber and the lensed fiber.
Figure 7:
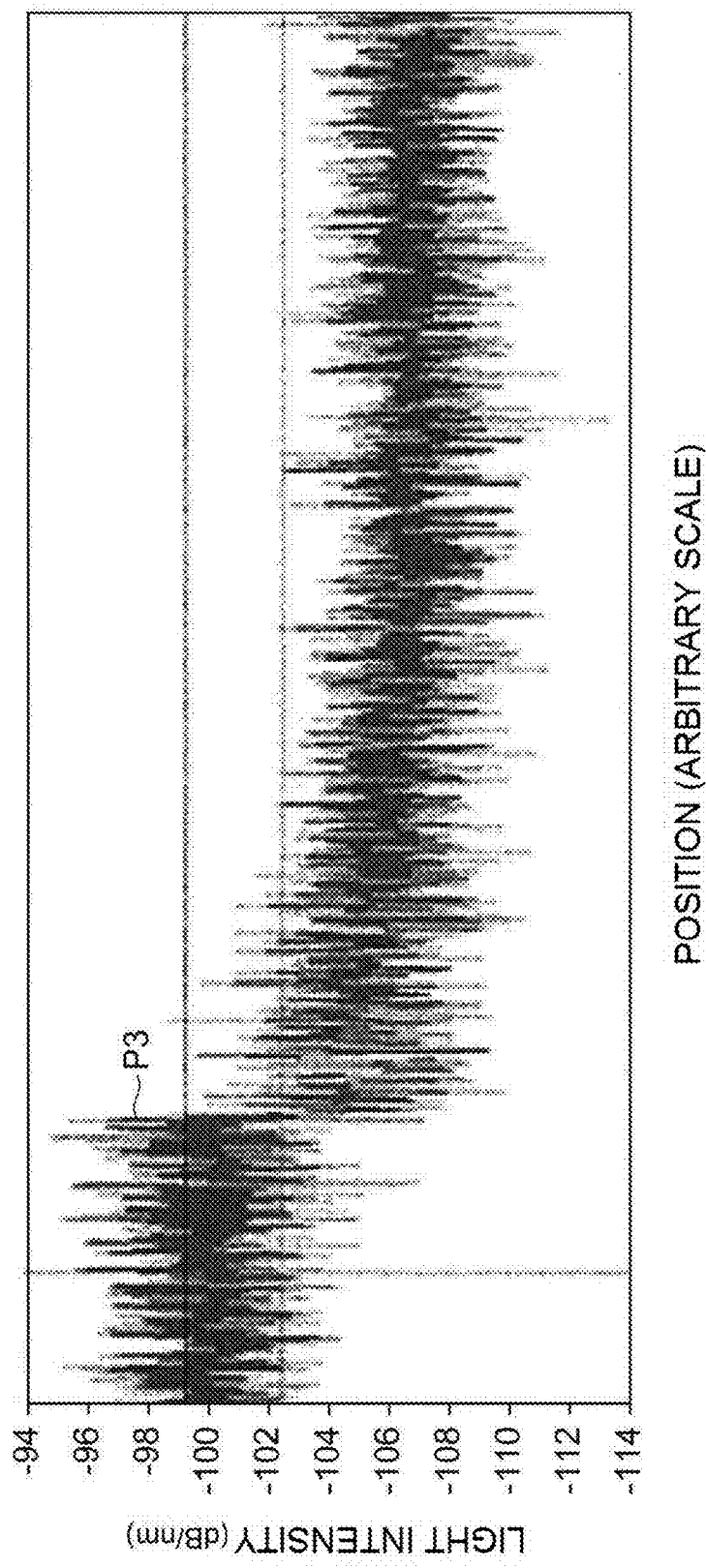
FIG. 7 is a graph representing reflected light intensity at the boundary portion between the optical fiber and the lensed fiber.
Figure 8:
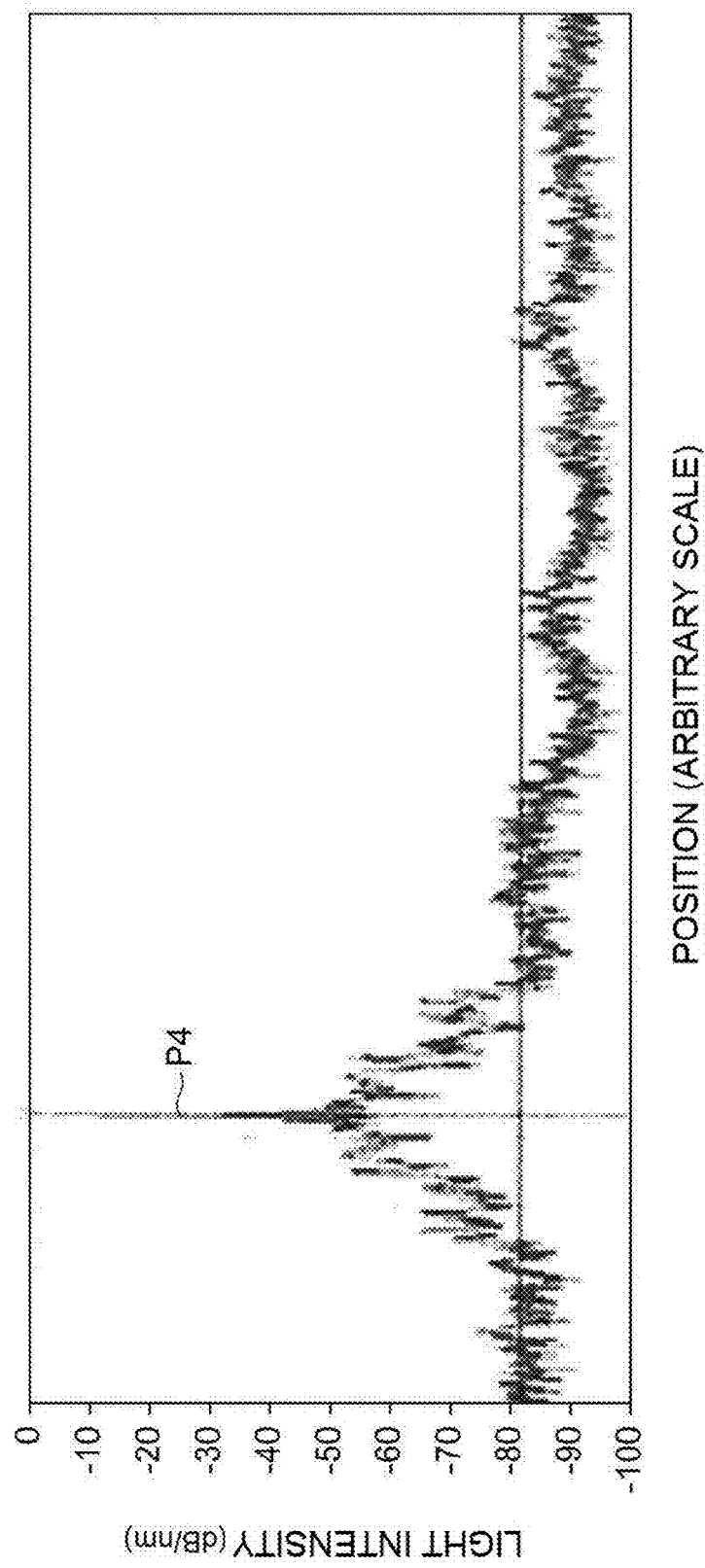
FIG. 8 is a graph representing the intensity of reflected light from an end face of the optical fiber when the optical fiber and the lensed fiber are not fusion spliced together.

FIGS. 5 to 7 are graphs representing the intensity of reflected light at the boundary portion between the optical fiber 22 and the lensed fiber 11 of the optical probe 10A. The vertical axis represents the reflected light intensity per unit wavelength [dB/nm] with respect to the Fresnel reflection intensity when the end face 22d of the optical fiber 22 is in contact with air (0 dB/nm). The horizontal axis represents the reflection position. In this measurement, the reflected light intensity was measured at the other end of the optical fiber 22. FIG. 5 shows a measurement result obtained after performing fusion splicing by one arc discharge. FIG. 6 shows a measurement result obtained when refractive-index-difference reduction processing was performed after fusion splicing. FIG. 7 shows a measurement result obtained when stronger refractive-index-difference reduction processing was performed. Specific examples of the refractive-index-difference reduction processing include increasing an arc discharge time, performing an additional arc discharge, and performing an arc discharge while moving a heating position. FIG. 8 is a graph representing, for comparison, the intensity of reflected light from an optical fiber end face when the optical fiber 22 and the lensed fiber 11 are not fusion spliced together.

Even when fusion splicing was performed by one arc discharge (FIG. 5), by appropriately controlling the arc discharge time, the refractive index adjusting material in the lensed fiber 11 was sufficiently diffused in the end part 22B of the optical fiber 22, and the intensity of reflected light (the peak P1 in FIG. 5) could be reduced to −70.02 dB/nm. When fusion splicing was performed with an additional arc discharge (FIG. 6), the amount of the refractive index adjusting material diffused in the end part 22B of the optical fiber 22 was increased, and the intensity of reflected light (the peak P2 in FIG. 6) could be reduced to −82.15 dB/nm. When fusion splicing was performed with a further additional arc discharge (FIG. 7), the amount of the refractive index adjusting material diffused in the end part 22B of the optical fiber 22 was further increased, and the intensity of reflected light (the peak P3 in FIG. 7) could be reduced to −89.84 dB/nm. The peak P4 shown in FIG. 8 corresponds to the Fresnel reflection (−14.7 dB) at the end face 22d of the optical fiber 22.

Figure 9:
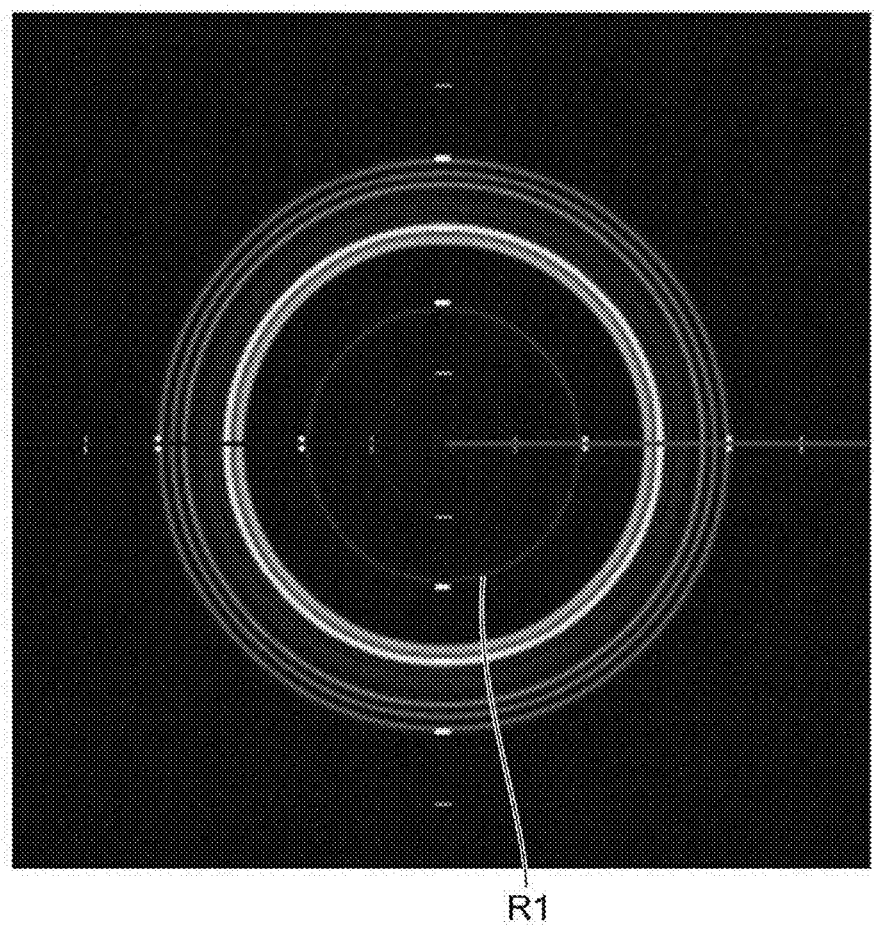
FIG. 9 shows an OCT measurement image.
Figure 10:
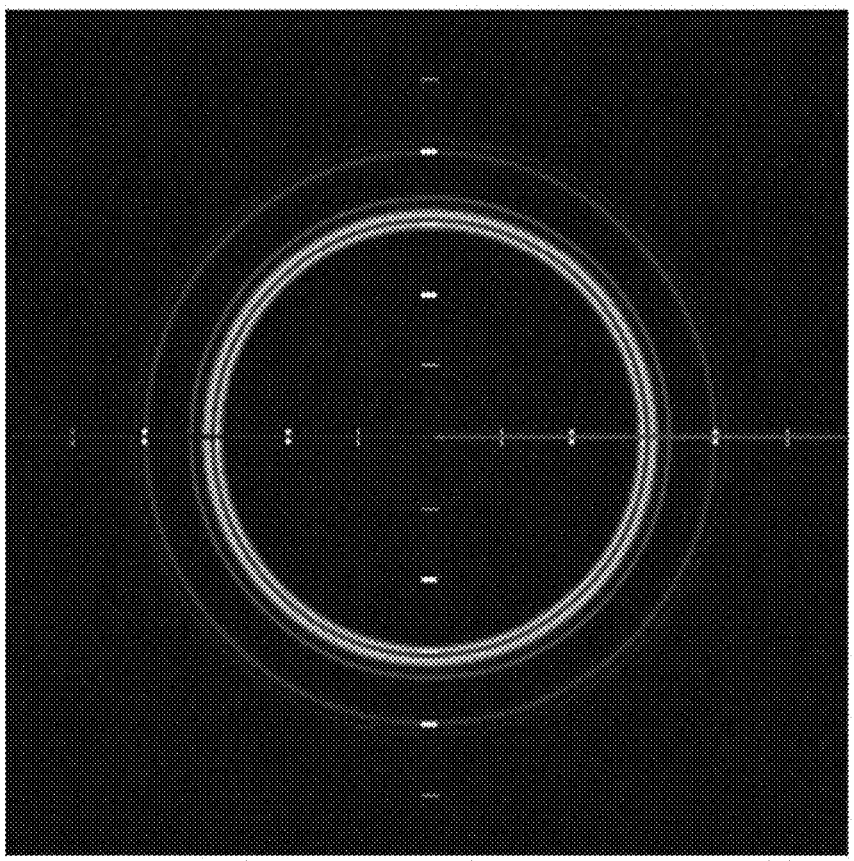
FIG. 10 shows an OCT measurement image.
Figure 11:
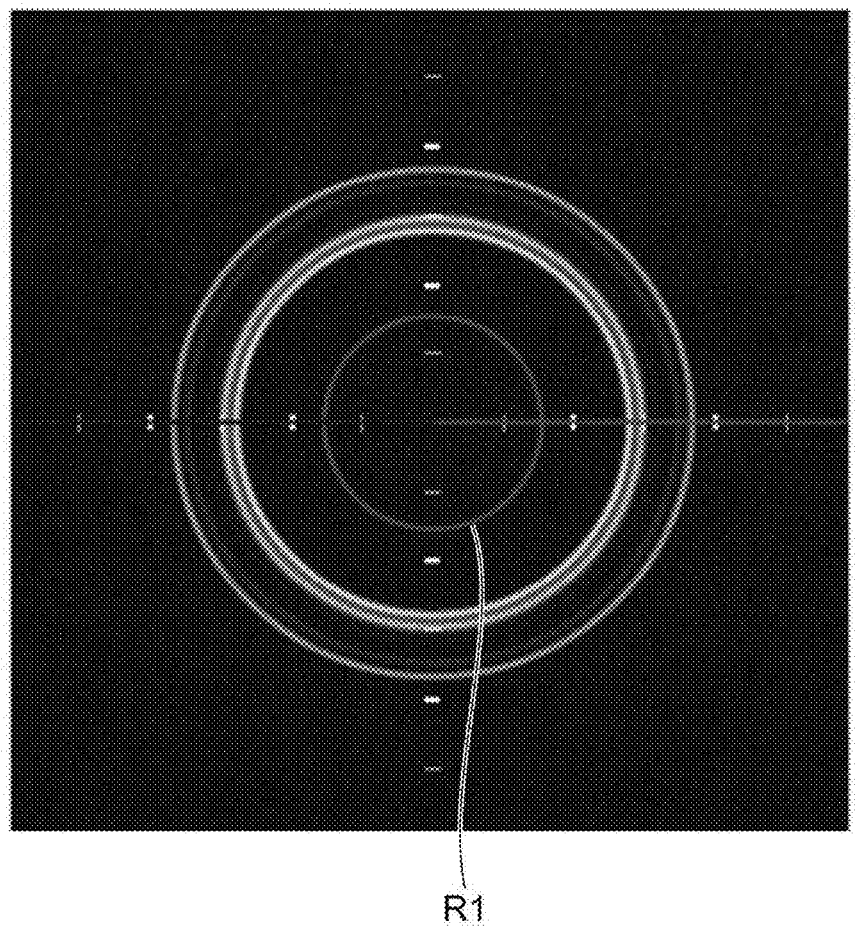
FIG. 11 shows an OCT measurement image.

FIGS. 9 to 11 show OCT measurement images. FIGS. 9 and 10 show OCT measurement images obtained by using the optical probe 10A. FIG. 9, which corresponds to FIG. 5, shows a measurement image after performing fusion splicing by an arc discharge, as a diffusing step in the present invention. FIG. 10 shows a measurement image after performing refractive-index-difference reduction processing in FIG. 7. FIG. 11 shows a measurement image when the optical fiber 22 and the lensed fiber 11 were fusion spliced together in a general arc discharge time, and the intensity of reflected light at the boundary portion between the optical fiber 22 and the lensed fiber 11 was −60 dB/nm. It can be seen that a ring R1, which represents the reflected light at the boundary portion, is clearly shown in FIG. 11, while the ring R1 is faint in FIG. 9 and is almost invisible in FIG. 10. In FIGS. 9 to 11, a plurality of rings existing outside the ring R1 represent reflected light at the boundary surface between the lensed fiber 11 and the cap 12 and the like.

Figure 12:
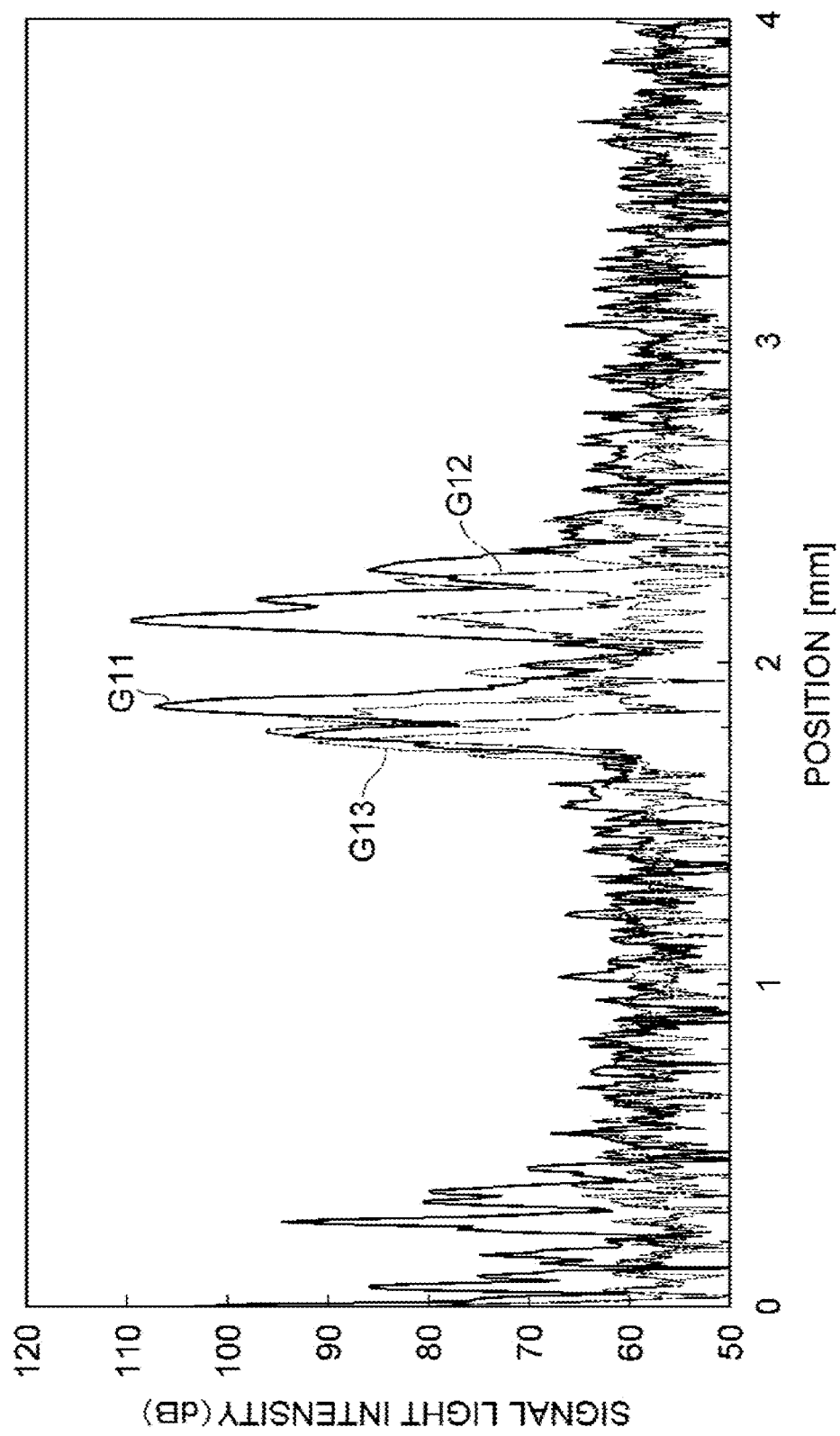
FIG. 12 shows graphs representing signal light intensities when refractive-index-difference reduction processing was performed.
Figure 13:
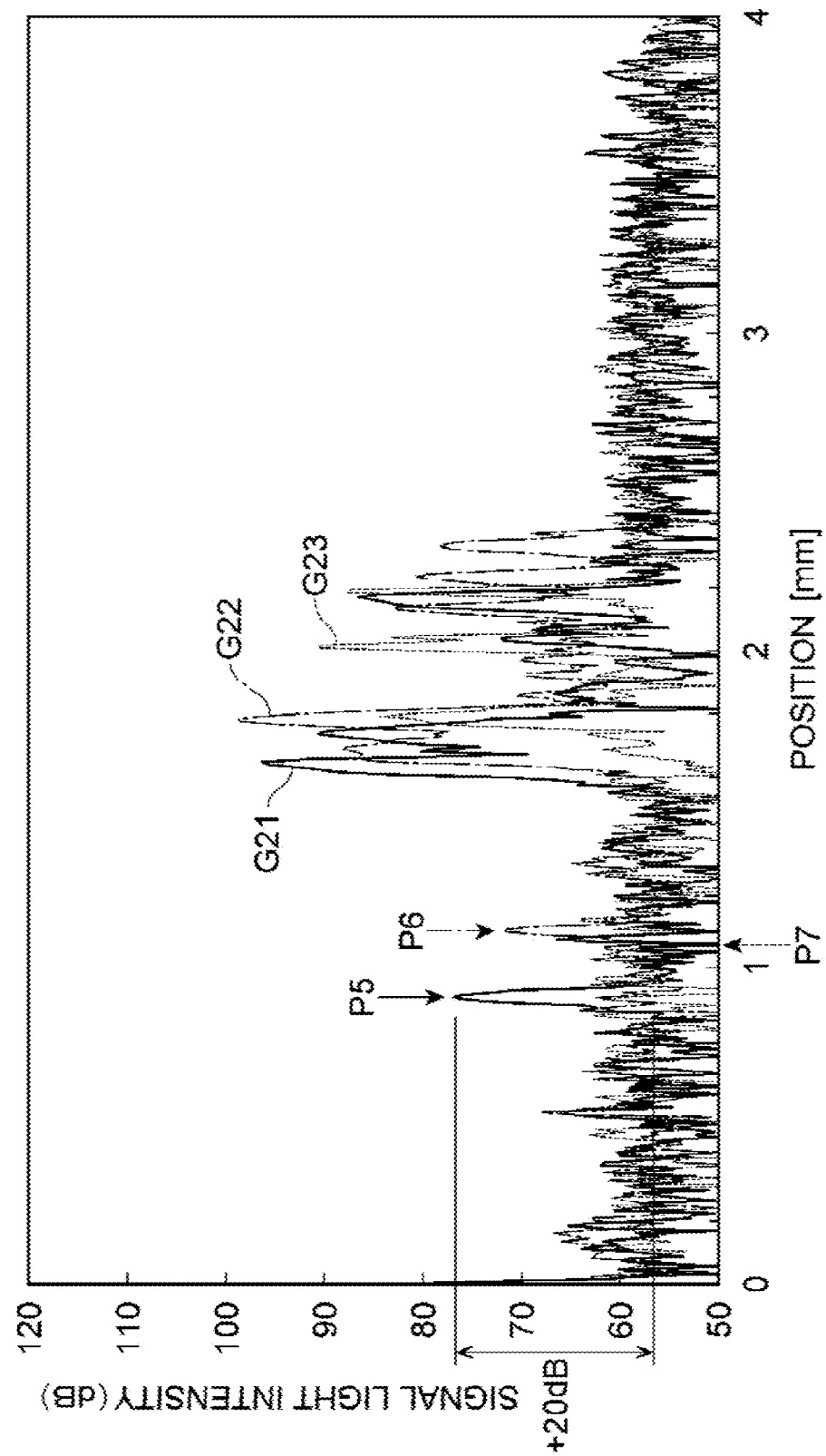
FIG. 13 shows graphs representing signal light intensities when refractive-index-difference reduction processing was not performed.

FIG. 12 shows graphs representing signal light intensity (a value obtained by signal-processing the reflected light intensity in the entire wavelength range used) when refractive-index-difference reduction processing was performed. FIG. 13 shows graphs representing signal light intensity when refractive-index-difference reduction processing was not performed. In FIGS. 12 and 13, the vertical axis represents the signal light intensity (dB), and the horizontal axis represents the position in the direction along the optical axis A. A position at about 1 mm on the horizontal axis approximately corresponds to the boundary portion between the optical fiber 22 and the lensed fiber 11. In FIG. 12, graphs G11 to G13 show the measurement results for three samples of the optical probe 10A. In FIG. 13, graphs G21 to G23 show the measurement results for other three samples of the optical probe 10A. In FIG. 13, it can be seen that peaks P5 to P7, which are greater than the intensity of background signal light by about 20 dB, occurred near the boundary portion. Such a peak is not observable in FIG. 12. Accordingly, it can be seen from these results that the intensity of reflected light at the boundary portion can be more effectively reduced by performing refractive-index-difference reduction processing.

Figure 14A:
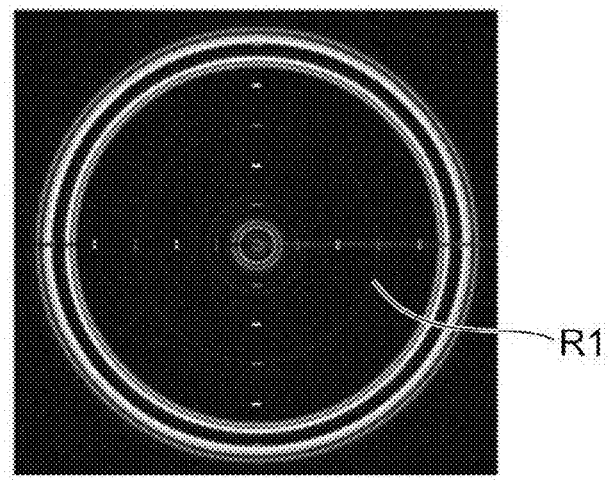
FIGS. 14A to 14C show OCT measurement images respectively corresponding to graphs G11 to G13 of FIG. 12.
Figure 14B:
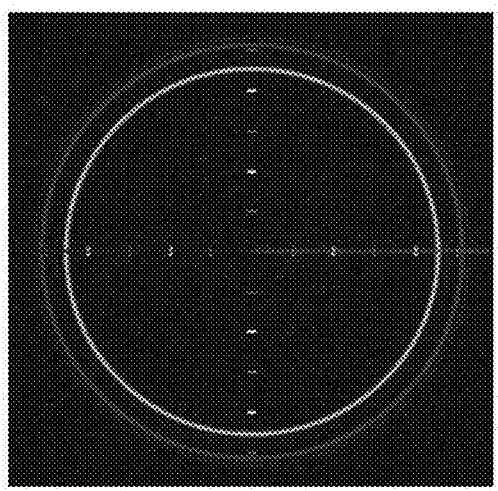
Figure 14C:
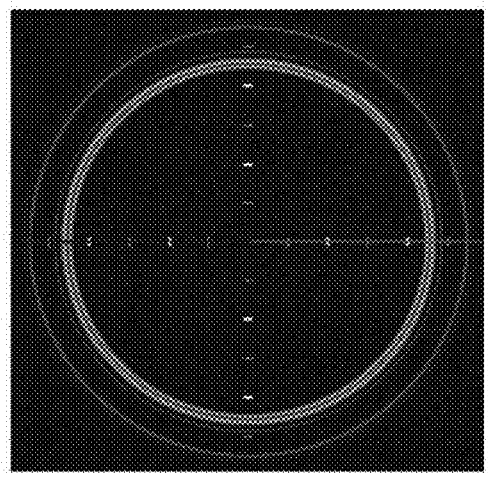
Figure 15A:
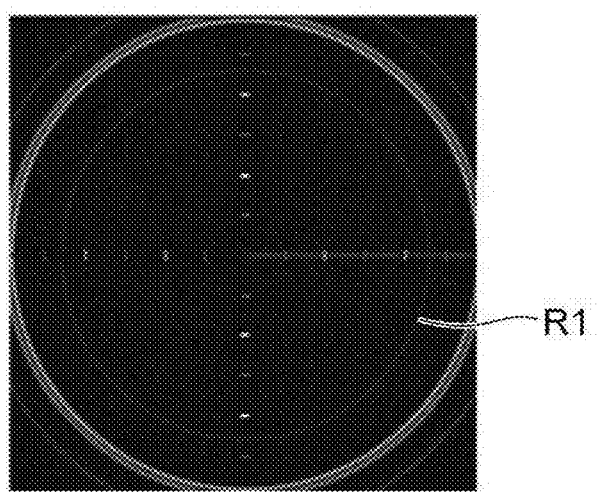
FIGS. 15A to 15C show OCT measurement images respectively corresponding to graphs G21 to G23 of FIG. 13.
Figure 15B:
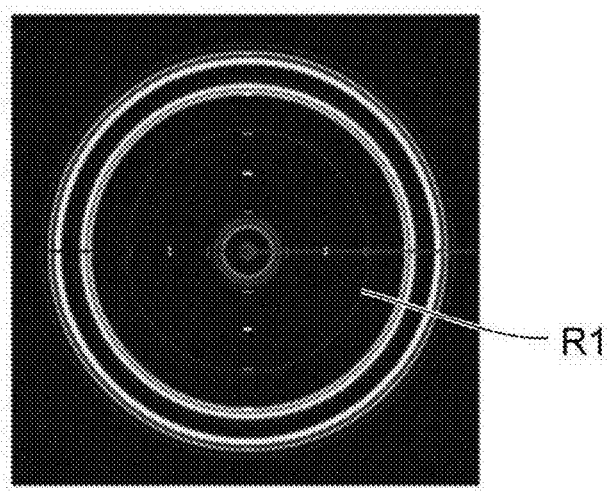
Figure 15C:
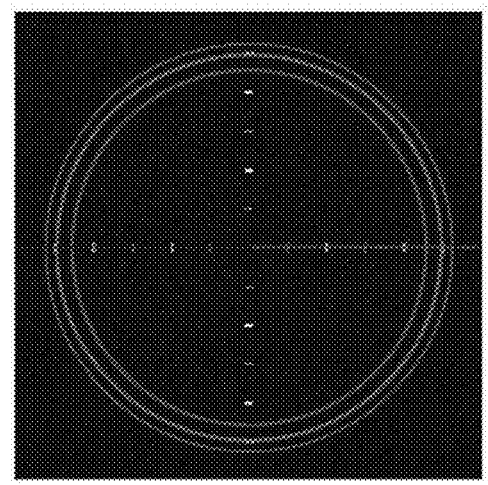

FIGS. 14A to 14C show OCT measurement images respectively corresponding to the graphs G11 to G13 in FIG. 12. FIGS. 15A to 15C show OCT measurement images respectively corresponding to the graphs G21 to G23 in FIG. 13. By comparing FIGS. 14A to 14C with FIGS. 15A to 15C, it can be seen that the ring R1, which represents the reflected light at the boundary portion and which is shown in each of FIGS. 15A to 15C, is faint in each of FIGS. 14A to 14C. From this, it can be seen that, by performing refractive-index-difference reduction processing when fusion splicing the optical fiber 22 and the lensed fiber 11 together, the amount of refractive index adjusting material diffused in the end part 22B of the optical fiber 22 is increased, and the intensity of reflected light can be more effectively reduced.

Figure 16:
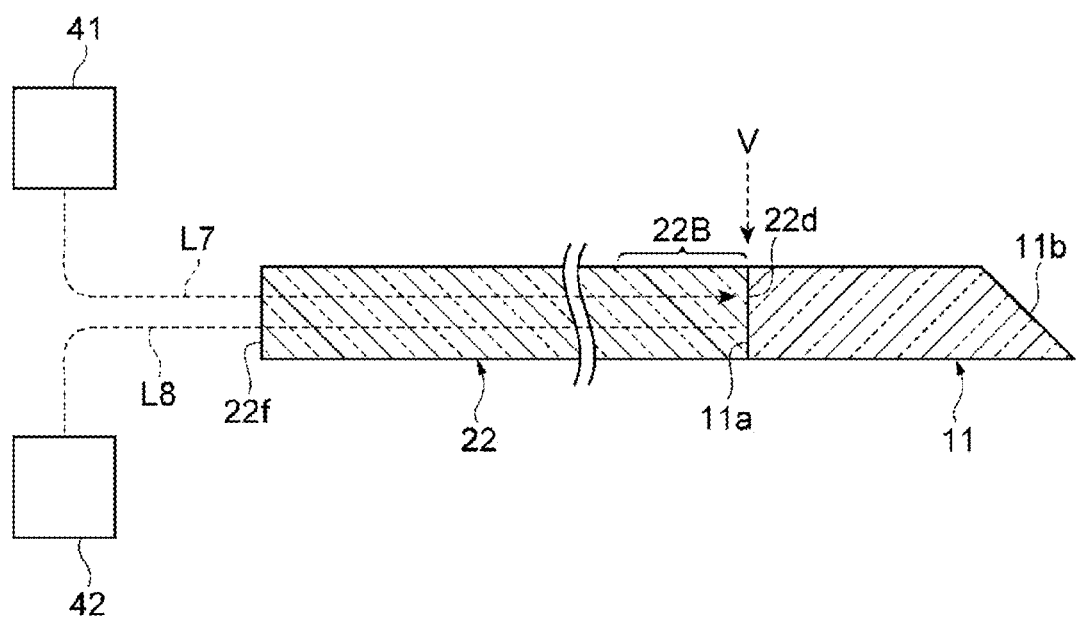
FIG. 16 is a conceptual diagram illustrating a step of fusion splicing the optical fiber and the lensed fiber together in the process of manufacturing the optical probe.

Next, a method of manufacturing the optical probe 10A will be described. FIG. 16 illustrates a step of fusion splicing the optical fiber 22 and the lensed fiber 11 together in the process of manufacturing the optical probe 10A. In this step, the end face 22d of the optical fiber 22 and the connecting surface 11a of the lensed fiber 11 are butted against each other and heated by performing an arc discharge V on the end faces 22d and 11a of these, and the end faces 22d and 11a are fused by the heat and spliced together. At this time, thermal diffusion is caused by the arc discharge, so that a refractive index adjusting material (Ge) included in the core region 11c of the lensed fiber 11 is diffused in the end part 22B of the optical fiber 22.

In the embodiment, in this step, a light-emitting device 41 and a light-detecting device 42 are optically coupled to the other end face 22f of the optical fiber 22. Then, test light L7 is emitted from the light-emitting device 41 into the other end face 22f of the optical fiber 22, and the optical fiber 22 and the lensed fiber 11 are fusion spliced together while measuring the intensity of reflected light L8 generated at the boundary portion between the optical fiber 22 and the lensed fiber 11 by using the light-detecting device 42. With the method of manufacturing the optical probe 10A according to the present embodiment, the temperature and the time for performing fusion splicing can be adjusted so that the intensity of reflected light at the boundary portion between the optical fiber 22 and the lensed fiber 11 decreases to desired intensity. Therefore, the reflected light generated at the boundary portion can be more effectively reduced.

An optical probe for optical coherence tomography and a method of manufacturing the optical probe according to the present invention can be modified in various ways. For example, a refractive index adjusting material may be diffused in the end part of the optical fiber before performing fusion splicing. A lensed fiber on which the deflecting surface 11b has not been formed and an optical fiber may be fusion spliced together, and subsequently the deflecting surface 11b may be formed. In the embodiments described above, various materials can be used as the refractive index adjusting material.

INDUSTRIAL APPLICABILITY

The present invention can be applied to various types of OCT, such as OCT for observing a blood vessel inner wall, OCT for ophthalmology, and the like.

The invention claimed is:

1. An optical probe for optical coherence tomography comprising:
   an optical fiber that includes a core region having a refractive index $n_1$ and that is configured to transmit irradiation light and back-scattered light; and
   a lensed fiber that includes a material for adjusting a refractive index, that has a refractive index $n_3$ on an optical axis of the lensed fiber, that is fusion spliced to one end of the optical fiber, that is configured to emit the irradiation light toward an object to be measured while collimating the irradiation light, and that is configured to collect and guide back-scattered light from the object to be measured to the one end of the optical fiber,
   wherein the refractive index $n_3$ is greater than the refractive index $n_1$, and the material is diffused in an end part of the optical fiber including the one end.

2. The optical probe for optical coherence tomography according to claim 1,
   wherein intensity of light reflected at a boundary portion between the one end of the optical fiber and the lensed fiber, the intensity being measured at the other end of the optical fiber, is less than −60 dB/nm with respect to Fresnel reflection intensity when the one end of the optical fiber is in contact with air.

3. The optical probe for optical coherence tomography according to claim 2,
   wherein the intensity of light reflected at the boundary portion is −80 dB/nm or less with respect to the Fresnel reflection intensity.

4. The optical probe for optical coherence tomography according to claim 1,
   wherein a refractive index of a core region of the optical fiber gradually becomes closer to a refractive index of the lensed fiber as a distance from the lensed fiber decreases.

5. The optical probe for optical coherence tomography according to claim 2,
   wherein a refractive index of a core region of the optical fiber gradually becomes closer to a refractive index of the lensed fiber as a distance from the lensed fiber decreases.

6. The optical probe for optical coherence tomography according to claim 3,
   wherein a refractive index of a core region of the optical fiber gradually becomes closer to a refractive index of the lensed fiber as a distance from the lensed fiber decreases.

7. A method of manufacturing the optical probe for optical coherence tomography according to claim 1, the method comprising:
   fusion splicing the one end of the optical fiber and the lensed fiber together; and
   diffusing the material included in the lensed fiber in the end part of the optical fiber by using heat generated in fusion splicing, while measuring intensity of light reflected at a boundary portion between the one end of the optical fiber and the lensed fiber at the other end of the optical fiber.

* * * * *